United States Patent [19]

Shibuya et al.

[11] Patent Number: 4,582,795

[45] Date of Patent: Apr. 15, 1986

[54] DEVICE FOR RAPID DIAGNOSIS OF DENTAL CARIES

[75] Inventors: Mutsumi Shibuya, Yokohama; Kiyoyuki Matsumoto, Hachioji, both of Japan

[73] Assignee: Showa Yakuhin Kako Co., Ltd., Kyobashi, Japan

[21] Appl. No.: 505,316

[22] Filed: Jun. 17, 1983

[30] Foreign Application Priority Data

Jun. 21, 1982 [JP] Japan ............................ 57-106389

[51] Int. Cl.$^4$ ...................... C12Q 1/04; G01N 21/78; G01N 33/52
[52] U.S. Cl. .......................................... 435/34; 422/56; 422/58; 422/61; 435/4; 435/29; 435/805; 436/165
[58] Field of Search ...................... 422/56, 57, 58, 61, 422/102; 435/4, 29, 805, 34; 128/743; 436/169, 63, 165

[56] References Cited

U.S. PATENT DOCUMENTS

| | | | |
|---|---|---|---|
| 3,785,930 | 1/1974 | Ellis | 435/805 |
| 3,846,247 | 11/1974 | Kronish et al. | 422/56 |
| 4,055,394 | 10/1977 | Friedman et al. | 422/56 |
| 4,359,455 | 11/1982 | Nakamura et al. | 435/4 |
| 4,450,844 | 5/1984 | Quisno | 128/743 |
| 4,473,079 | 9/1984 | Jasper et al. | 422/56 X |

OTHER PUBLICATIONS

Shimono et al., The Japanese Journal of Pedodontics, vol. 18, No. 3, pp. 606-611, 1980.
Nakamura et al., Journal of Dental Health, vol. 30, No. 4, pp. 70-75, 1980.

Primary Examiner—Arnold Turk
Assistant Examiner—Robert J. Hill Jr.
Attorney, Agent, or Firm—Bucknam and Archer

[57] ABSTRACT

A method and device for rapid diagnosis of dental caries are provided in which a very small amount of saliva to be tested is impregnated into a test piece containing a dry reagent. The test piece is supported on a coating film, whereby the test piece can be maintained with the air intercepted to prevent evaporation of saliva for about 15-30 minutes at a temperature around 20°-37° C., and a color change of the reagent due to the enzymatic reaction of the dental caries-causing microorganism is examined.

6 Claims, 3 Drawing Figures

DEVICE FOR RAPID DIAGNOSIS OF DENTAL CARIES

BACKGROUND OF THE INVENTION

In judging an attack of a dental disease or caries degree in the dental clinic or from oral hygiene, various methods have been reported for examining the activity and number of germs of microorganisms such as *Streptococcus mutans* (hereinafter referred to as *S. mutans*) and *Lactobacillus* in saliva in the mouth or dental plaque on the teeth. Previously, a rapid method of the diagnosis has been based on the fact that microorganisms cause change in color of a specified reagent (see the specification of Japanese Pat. No. 539011 (Japanese patent application publication No. 19817/1968) in which the tests are made on general microorganisms). The method of this patent comprises, in summary, adding a given amount of (a) resazurin, (b) a neotetrazolium chloride or (c) triphenyltetrazolium chloride to a culture liquid (nutrient source for the propagation of microorganisms); immersing the test paper in the liquid; drying the test paper; dividing the test paper into small test pieces; dropping a given amount of a germ suspension to be tested on the test piece; culturing the same at 37° C. for a given time; and judging the activity of the germs in the germ suspension from a change in color tone.

Various methods of determining caries activity have also been reported. A recent report of Tsutomu Shimono et al. ("The Japanese Journal of Pedodontics" 18, (3), 606-611 (1980) may be summarized as follows: dental plaque in the mouth is suspended in a physiological saline solution. A given volume (0.1 ml) of the suspension is used as a sample. Separately, a solution containing 10% of sucrose, 0.006% of bromthymol blue (B.T.B.) and 0.05% of sodium azide ($Na_3N$) and having pH 7.2 is prepared. The sample is inoculated to the solution and the mixture is allowed to stand at 37° C. for 30 min. The color tone of the solution is changed from yellowish green (negative) to light yellow green (false-positive) and then to yellow (positive). It is described therein that as compared with the results of conventional methods of culture tests carried out simultaneously with the above-mentioned Shimono's test, a high positive relationship to the degree of children's dental caries was recognized. Masakazu Nakamura et al. reported a method of diagnosis by an examination of mouths of kindergarten pupils and results thereof in "Journal of Dental Health" 30 (4) published in December, 1980. They used resazurin, methyl red, alizarin red S, lacmoid, bromocresol green or bromophenol blue as the color indicator. A given volume of a suspension of dental plaque in physiological saline solution was added to a culture liquid comprising 0.003% of the above color indicator, together with 10% of sucrose and 0.05% of $Na_3N$. After effecting the culture at 37° C. for 30 min, the teeth-decaying activity was judged from a change in color tone of the culture liquid. They reported that the results had a high positive relationship with the rate of dental caries of the kindergarten pupils. It is further disclosed therein that the most clear change in color tone was recognized when resazurin was used. It has been recognized in various reports that resazurin is thus an effective indicator in the determination of teeth-decaying activity. These methods can be carried out easily. However, they are all wet methods wherein saliva or dental plaque is added to a small amount of a color-developing liquid containing resazurin or a pH indicator, the mixture is warmed to 37° C. and a color change after 30 min is examined. Actually, these methods have not been generalized clinically. The most ordinary conventional technique of examining teeth-decaying activity comprises mixing 0.1-0.2 ml of saliva or mixing dental plaque with about 3 ml of a culture medium and culturing the same in an incubator at 37° C. for 24-72 h. This is a wet method. This method has been employed throughout our country.

SUMMARY OF THE INVENTION

The present invention relates to a method and device for rapid diagnosis of teeth-decaying activity of a subject or a patient in the prevention or treatment of dental caries.

After investigations made for the purpose of developing a method for prompt determination of the teeth-decaying activity with resazurin in a short time, the inventors have attained a dry method. Thus, an object of the present invention is to provide a method and a device for rapid diagnosis of teeth-decaying activity of teeth-decaying microorganisms contained in saliva or dental plaque in a short time by using a dry test piece, e.g. paper test piece, containing a color-indicator composition.

DESCRIPTION OF THE PREFERRED EMBODIMENT

Figure 1:
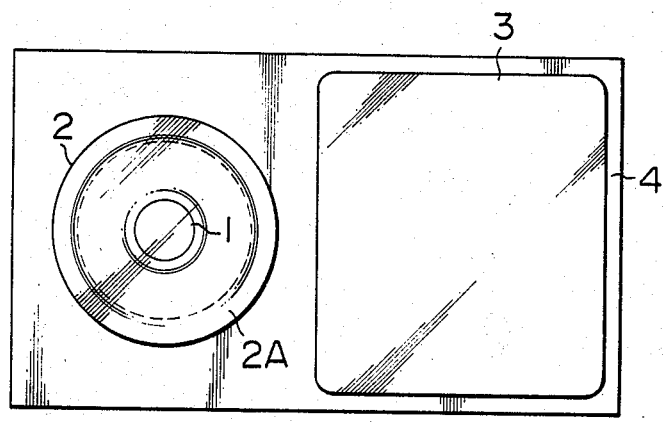
FIG. 1 is a plan view showing the diagnostic device of the present invention.

In FIG. 1 showing an embodiment of the diagnostic device of the present invention, the symbol 1 indicates a small, round paper piece having a diameter of 5-10 mm or square paper piece having sides of at least 4 mm which piece has been impregnated with the reagent solution. The small paper piece is made of a generally used filter paper having a thickness of preferably up to 0.8 mm. The paper piece is covered with a coating film 2. An adhesive has previously been applied to a periphery 2A on the inner surface of the coating film 2. A supporting film 3 is arranged next to them and adhered peelably to a ground paper 4. In many cases, it is convenient for handling in the test to apply the adhesive to the whole inner surface of the coating film so that one surface of the small paper piece is fixed firmly to the inner surface of the coating film. By being arranged in the above manner, the small test piece 1 is completely kept from the open air or air circulation and maintained under a germ-free condition before use. The supporting film 3 is a round film having a diameter of 5-10 cm or square or rectangular film having nearly the same area. As the film 2, there may be mentioned a round film having a diameter of 3-5 cm or a square film having nearly the same area. The size of the ground paper is such that both films 2 and 3 may be arranged side by side thereon. These films may be made of transparent organic resins or transparent plastics.

The reagent solution to be used for the impregnation of the small paper piece 1 is an aqueous solution of a reagent composition comprising 10 wt.% of sucrose and 0.05-0.003 wt.% of an indicator which is resazurin, triphenyltetrazolium, neotetrazolium, 2,6-dichlorophenol indophenol, methyl orange and a salt thereof (preferably 0.003 wt.% of resazurin). Resazurin is used as a color indicator in this case. As described above, the teeth-decaying activity of, for example, S. mutans can be determined promptly, though indirectly, from a change in color tone of the indicator. More particularly, the saliva and dental plaque contain large amounts of S. mutans and lactic acid bacteria which have been considered to be main causes for teeth decay. Particularly, enzymes of S. mutans introduce sucrose condensation to form glucan (dextrin) in the culture liquid. The sugar is enzymatically decomposed to form lactose. It is considered that the color tone of resazurin is changed by the active enzymatic reaction, change in oxidation-reduction potential and liquidity reduction. The change in color tone is, for example, as follows: purple→bluish red→red.

The inventors have studied the color change of resazurin due to the pH change in the color reaction. pH of the sucrose-containing solution is not lowered to below 6. The change in color tone by S. mutans or saliva from bluish purple to red is due to a color change of resazurin in the oxidation-reduction reaction system. The mechanism of this phenomenon may be explained as follow: resazurin has the maxium absorption at the wave length ($\lambda_{max}$) of 603 nm in the visible ray absorption spectrum (fluorescence wave length in fluorescence spectrum ($\lambda_{em}$): 630 nm). Resazurin is converted into resorufin (having the maximum absorption at wave length of 573 nm; red) of the following chemical structure:

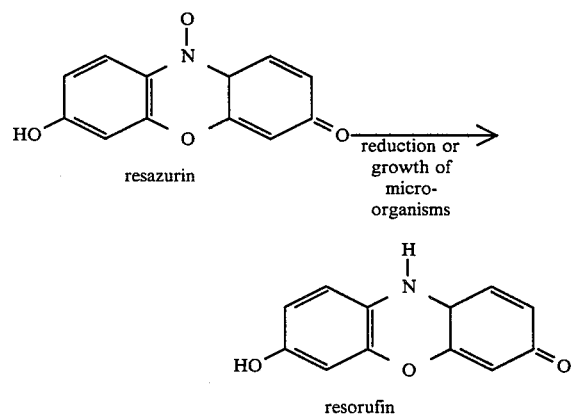

by the growth of the microorganisms or in the presence of a reducing agent.

|  | Resazurin | Resorufin |
| --- | --- | --- |
| $\lambda$ max | 603 nm | 573 nm |
| $\lambda$ em | 630 nm | 590 nm |
| Color tone | Bluish purple | Red |

It has been made apparent in the present invention that the change in color tone of the resazurin indicator by S. mutans in the saliva in the culture medium is caused not by pH change but by the oxidation reduction reaction, since the above $\lambda_{max}$ and $\lambda_{em}$ are different from values determined by the color change due to pH change. The change in color tone could be made clearer by adding a dispersing agent such as polyvinyl alcohol thereto. As shown in examples given below, a relationship is observed between the change in color tone and the teeth-decaying activity. Therefore, the teeth-decaying activity can be determined from the change in color tone. If a device is prepared as above except that triphenyltetrazolium chloride is used as the indicator, the color tone is changed from red to colorless. This color change indicates a change of negative teeth-decaying activity to positive teeth-decaying activity. In case in which methyl orange is used as the indicator, the color tone is changed from yellowish green to reddish yellow. This color change indicates a change from negative teeth-decaying activity to positive teeth-decaying activity. Among these indicators, resazurin exhibits the most clear change in color tone. In this case, the color is changed stepwise. This change can be recognized readily with the naked eye. Therefore, resazurin is used as the preferred indicator in the present invention.

The adhesive to be applied to the film 2 comprises mainly a synthetic rubber. The adhesive should be easily removable from the supporting film 3 and the ground paper 4 at ambient temperature and capable of adhering again to a material of a heater, i.e. material of the heater used for the culture, such as a metal, wood or plastic, together with the small paper piece. More particularly, the small paper piece impregnated with saliva or dental plaque dental caries causing microorganisms should be cultured at 37° C. for 10-15 min. while the air supply is intercepted as far as possible and the evaporation of water in the saliva is prevented. The device of the present invention is such an easy, small device that it may be heated by applying the same including the film to the surface of the human skin as a substitute for the material of the heater. It is desirable, therefore, to select an adhesive harmless to the human skin as the adhesive for the film. In case the supporting film 3 is not applied to the surface of the heater or human skin but kept in the heater, the supporting film 3 may be used in adhesive-free state.

Figure 2:
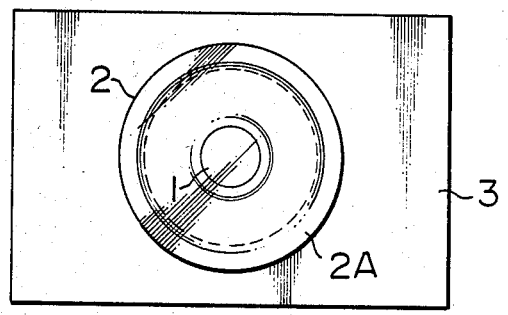
FIG. 2 is a plan view of the device of FIG. 1 when the test piece containing a liquid sample and the coating film are both supported on the supporting film.

In using the diagnostic device of the present invention, a very small amount, generally one drop, of the saliva is taken by means of a dropping pipette or the like; the film 2 is peeled halfway from the ground paper in the device; the saliva is dropped from the pipette on the small paper piece 1; the saliva is left to spread sufficiently uniformly; then the film 2 covering the small paper piece 1 is applied to the supporting film 3 together with the paper piece 1. A case wherein the adhesive is applied to only the periphery on the inner surface of the film 2 is shown in FIG. 2. The supporting film 3 supporting the paper piece 1 and coating film 2 is peeled off from the ground paper 4 together with the piece 1 and film 2; they are then applied to the surface of a heater or an exposed part of human body as a substitute for the heater and a change in color tone of the small paper piece 1 is examined after 15 min. The teeth-decaying activity is judged to be negative, weakly positive or positive according to the change in color tone (blue→ purplish red→red, respectively). A characteristic feature of the device of the present invention is that human body temperature can be employed as a substitute for the heater for maintaining the culture temperature of around 37° C.

Figure 3:
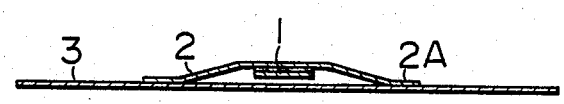
FIG. 3 is a side view of FIG. 2.

In the case in which the adhesive is applied to the whole inner surface of the coating film 2, the back of the small paper piece 1 is exposed when the film 2 is peeled off halfway since the surface of the paper piece 1 is closely adhered to the film 2. Accordingly, the saliva is applied to the exposed back. After the impregnation with the saliva, the small paper piece 1 is peeled off from the ground paper 4 together with the film 2 and they are applied to the supporting film 3 to attain a state shown in FIG. 3. They (including the supporting film 3) are peeled off from the ground paper 4 and applied to the surface of a heater or an exposed part of human body as a substitute for the heater. If they are not applied to the heater but placed in a heater, it is possible to place all of them including the ground paper 4 in the heater without peeling the supporting film 3 from the ground paper 4.

Thus, by using the device for diagnosing dental caries of the present invention, it becomes possible to determine teeth-decaying activity easily in a short time in not only the treatment of patients but also prevention and countermeasure for the treatment of infants. Further, the device can be produced easily and supplied at a low cost.

The following example will further illustrate the present invention.

EXAMPLE

A piece of filter paper having 8 mm diameter was immersed in an aqueous solution containing 0.025 wt.% of resazurin and 10 wt.% of sucrose and it was dried to obtain a small paper piece 1 (disk) for use for the diagnosis. The paper piece 1 was covered with a transparent plastic coating film 2 of 4 cm diameter. The coating had an adhesive layer applied to the whole inner surface thereof. They were applied to a rectangular ground paper 4 having the size of 5 cm × 10 cm. A square of 4.5 cm × 4.5 cm transparent plastic supporting film 3 having an adhesive layer on the back thereof was applied to the same ground paper neighboring the coating film 2. The resulting product was placed in a transparent plastic packing sachet or a small polymer bag and heat-sealed to obtain a final product for single usage.

Tests

Saliva of each subject was taken in a miniature cup. A drop (about 0.05 ml) of the saliva was taken out therefrom by means of a plastic dropping pipet and applied to the blue disk (small paper piece) 1 exposed by peeling the film 2 off or taken out from the device of the present invention. After leaving them to stand for effecting the sufficient impregnation, they were applied to the supporting film 3. They were peeled off from the ground paper 4 and applied to an arm of the subject. Fifteen minutes later, a change in color tone of the disk 1 was examined. The results are shown in Table 1 in comparison with the results of conventional ST media method and mitis salivalius bacitracin broth (MSBB) method.

TABLE 1

| Group (Note 1) | Subject (adult) No. | Sex | Age | Judgement according to the present invention (Note 2) | ST media method (Note 3) | MSBB method (Note 4) |
|---|---|---|---|---|---|---|
| A | 1 | male | 35 | +++ | ++ | +++ |
|   | 2 | male | 34 | +++ | + | +++ |
|   | 3 | female | 23 | +++ | ++ | +++ |
|   | 4 | male | 24 | +++ | + | +++ |
|   | 5 | female | 52 | +++ | ++ | +++ |
|   | 6 | male | 27 | +++ | + | +++ |
| B | 7 | male | 25 | + | + | ++ |
|   | 8 | male | 24 | ++ | − | ++ |
|   | 9 | male | 40 | + | − | ++ |
|   | 10 | female | 24 | − | − | − |
|   | 11 | female | 23 | + | + | +++ |
|   | 12 | male | 28 | − | − | ++ |
| C | 13 | female | 28 | + | + | ++ |
|   | 14 | female | 31 | − | − | + |
|   | 15 | female | 24 | − | − | − |
|   | 16 | female | 23 | − | − | − |
|   | 17 | male | 45 | − | − | − |
|   | 18 | male | 27 | + | − | − |

Note 1: Conditions of dental caries of the respective patients were classified into three ranks of A (serious), B (moderate) and C (good) by exploration by dentists.
Note 2: The conditions of dental caries were judged to be as follows from degrees of color change of the diagnostic device: colorless or red (+++) (serious); faint red, light red or red (+ or ++) (not serious); purple or blue (−) (healthy).
Note 3: A commercially available set for testing teeth-decaying activity (ST Media ®; a product of Showa Yakuhin Kako Co., Ltd.). Teeth-decaying microorganism and acid-producing microorganisms in saliva sample were determined form pH reductionusing this set.
Note 4: MSBB (trade name "Mucount" (mitis salivarius bacitracin medium of Show Yakuhin Kako Co., Ltd.); a selective broth for Streptococcus mutans which causes dental caries.

It is evident that the device of the present invention is effective for the rapid diagnosis of teeth-decaying activity in a short time.

We claim:

1. A device for rapid diagnosis of dental caries in saliva of a patient by means of a reagent which changes color in the presence of dental caries or dental caries-causing microorganisms comprising a piece of ground paper, a supporting film peelably adhered by an adhesive layer backing to the ground paper in a first region, a coating film having an inner surface and an adhesive layer at least around the periphery of the inner surface of said coating film, a piece of filter paper which has been impregnated with a solution containing a reagent which changes color in the presence of dental caries or dental caries-causing microorganisms and then dried, said piece of filter paper being supported on said inner surface of said coating film, said coating film being peelably adhered by its adhesive layer to the ground paper in a second region in such a manner that said piece of filter paper is completely kept from open air or air circulation and is maintained in a germ-free condition, said first and second regions being side by side on said ground paper, whereby the coating film may be peelable detached from the piece of ground paper, a saliva sample placed on the piece of filter paper, the coating film peelably adhered to the supporting film in such a manner that an airtight seal is formed between said coating film and said supporting film so as to preclude evaporation of the saliva sample placed on said piece of filter paper, and said supporting film attached to skin of a patient for incubation purposes.

2. The device according to claim 1, wherein said adhesive layer of said coating film is over the entire inner surface of said coating film.

3. The device according to claim 1, wherein the reagent contains 10 weight % of sucrose and 0.05–0.003 wt.% of an indicator which is a member selected from the group consisting of resazurin, triphenyltetrazolium, neotetrazolium, 2,6-dichlorophenol, indophenol, methyl orange and a salt thereof.

4. The device according to claim 1, wherein said supporting film is made of a transparent organic resin or a transparent plastic material.

5. The device according to claim 1, wherein said piece of filter paper is round, square or rectangular.

6. The device according to claim 1, wherein said supporting film is peelable from said ground paper at room temperature and adheres to a surface by warming.

* * * * *